(12) United States Patent
Getsay et al.

(10) Patent No.: US 9,963,110 B2
(45) Date of Patent: May 8, 2018

(54) SYSTEM FOR ASSISTING WITH VEHICLE TRAFFIC STOPS

(71) Applicants: James G. Getsay, Harmony, PA (US); Christina Knox, Harmony, PA (US)

(72) Inventors: James G. Getsay, Harmony, PA (US); Christina Knox, Harmony, PA (US)

(73) Assignee: INVEX, LLC, Zelienople, PA (US)

( * ) Notice: Subject to any disclaimer, the term of this patent is extended or adjusted under 35 U.S.C. 154(b) by 29 days.

(21) Appl. No.: 14/948,771

(22) Filed: Nov. 23, 2015

(65) Prior Publication Data

US 2017/0144631 A1 May 25, 2017

(51) Int. Cl.
| | |
|---|---|
| *B60R 1/06* | (2006.01) |
| *B60R 99/00* | (2009.01) |
| *G01N 33/497* | (2006.01) |
| *G06K 7/08* | (2006.01) |
| *G06K 7/14* | (2006.01) |
| *H04N 5/33* | (2006.01) |
| *B60R 19/48* | (2006.01) |

(52) U.S. Cl.
CPC .............. *B60R 99/00* (2013.01); *B60R 19/48* (2013.01); *G01N 33/4972* (2013.01); *G06K 7/087* (2013.01); *G06K 7/1413* (2013.01); *H04N 5/33* (2013.01)

(58) Field of Classification Search
CPC ...................................................... B60R 1/06
USPC .............. 701/49; 116/63 P; 340/908, 908.1; 901/15
See application file for complete search history.

(56) References Cited

U.S. PATENT DOCUMENTS 5,038,136 A * 8/1991 Watson ............... B60Q 1/50
116/50
5,294,138 A * 3/1994 Yang ................. G08G 1/0955
116/63 P (Continued)

FOREIGN PATENT DOCUMENTS

WO WO-2008033029 A1 * 3/2008 ......... H05B 37/0227

OTHER PUBLICATIONS

An improvement on a teleoperation system of robot arm with visual servo mechanism by target selection; Yoshitaka Matsuda et al., 2012 Proceedings of SICE Annual Conference (SICE);Year: 2012; pp. 1579-1584; Referenced in: IEEE Conference Publications.*

(Continued)

*Primary Examiner* — Cuong H Nguyen
(74) *Attorney, Agent, or Firm* — Eckert Seamans; Stephen Bucchianeri; Philip Levy

(57) ABSTRACT

A system for assisting with vehicle traffic stops wherein a first vehicle stops a second vehicle is provided. The system includes a control system structured to be operative from within the first vehicle and an arm assembly structured to be coupled to the first vehicle. The arm assembly includes a telescoping arm member, a drive system, and a remote assembly coupled to a distal end of the arm member. The remote assembly includes a number of electronic devices for (i) collecting information at or from a location adjacent the remote assembly and providing the information to the control system and (ii) enabling two-way communication between the first vehicle and the location, wherein the arm member is structured to be selectively elongated and retracted by the drive system under control of the control system.

26 Claims, 14 Drawing Sheets

(56) References Cited

U.S. PATENT DOCUMENTS

| | | | |
|---|---|---|---|
| 5,623,205 A | | 4/1997 | Tomita et al. |
| 5,652,705 A | * | 7/1997 | Spiess .................... G08G 1/164 |
| | | | 701/117 |
| 6,864,784 B1 | * | 3/2005 | Loeb ................ G08G 1/0967 |
| | | | 16/180/171 |
| 7,275,889 B1 | | 10/2007 | McGill |
| 7,421,334 B2 | * | 9/2008 | Dahlgren ............... G07C 5/008 |
| | | | 340/989 |
| 7,896,113 B1 | | 3/2011 | Ramirez |
| 7,902,998 B2 | * | 3/2011 | Wheaton ................... G09F 7/18 |
| | | | 340/908 |
| 8,164,483 B1 | * | 4/2012 | Phillips .................. E01F 9/681 |
| | | | 116/63 P |
| 8,970,363 B2 | * | 3/2015 | Kraimer ............. B60R 21/0132 |
| | | | 172/2 |
| 9,122,276 B2 | * | 9/2015 | Kraimer ............... G05D 1/0016 |
| 9,227,568 B1 | * | 1/2016 | Hubbell .................. B60R 1/081 |
| 2002/0036565 A1 | | 3/2002 | Monroe |
| 2003/0070603 A1 | * | 4/2003 | Vandermolen ........... B60Q 1/50 |
| | | | 116/28 R |
| 2003/0081934 A1 | * | 5/2003 | Kirmuss ................ B60R 11/02 |
| | | | 386/224 |
| 2005/0017491 A1 | | 1/2005 | Mein |
| 2005/0065711 A1 | * | 3/2005 | Dahlgren ............... G07C 5/008 |
| | | | 701/117 |
| 2007/0030350 A1 | | 2/2007 | Wagner |
| 2007/0228755 A1 | | 10/2007 | Alvarado et al. |
| 2008/0106908 A1 | * | 5/2008 | Englander ............... B60Q 1/24 |
| | | | 362/481 |
| 2008/0204276 A1 | * | 8/2008 | Wheaton ................... G09F 7/18 |
| | | | 340/908 |
| 2009/0080096 A1 | * | 3/2009 | Fimeri ...................... B60R 1/07 |
| | | | 359/841 |
| 2010/0001652 A1 | * | 1/2010 | Damsleth ........... H05B 37/0227 |
| | | | 315/149 |
| 2014/0195057 A1 | * | 7/2014 | Zerhusen ............. A47B 23/046 |
| | | | 700/275 |
| 2014/0270383 A1 | | 9/2014 | Pederson |
| 2015/0296117 A1 | | 10/2015 | Johnson |
| 2015/0334345 A1 | | 11/2015 | Fichera |

OTHER PUBLICATIONS

Envirobot A bio-inspired environmental monitoring platform; Behzad Bayat; Alessandro Crespi; Auke Ijspeert ; 2016 IEEE/OES Autonomous Underwater Vehicles (AUV); Year: 2016, IEEE Conferences; pp. 381-386.*

Mobile dual arm robot for automated order picking system in warehouse containing various kinds of products; Fumiko Beniyama et al.; 2015 IEEE/SICE Inter.Symposium on System Integration (SII); Year: 2015; pp. 332-338; IEEE Conferences.*

Novel design and performance analysis of a Mars exploration robot; Benazir Bashar Riddhe et al.; 2017 Third Inter Conf on Research in Computational Intelligence and Communication Networks (ICRCICN); Year: 2017; pp. 132-136 IEEE Conferences.*

Wireless Power Transfer for Electric Vehicle Using an Adaptive Robot; O. A. Mohammed et al.; IEEE Transactions on Magnetics Year: 2017, vol. 53, Issue: 6; Article Sequence No. 7205404; IEEE Journals & Magazines.*

* cited by examiner

SYSTEM FOR ASSISTING WITH VEHICLE TRAFFIC STOPS

BACKGROUND OF THE INVENTION

1. Field of the Invention

The present invention pertains to vehicle traffic stops performed by, for example and without limitation, police officers, and, in particular, to a system for assisting with such vehicle traffic stops that enables the stop to be conducted without requiring the police officer to leave his or her vehicle.

2. Description of the Related Art

A traffic stop is initiated when a police officer observes a motorist failing to abide by one or more traffic laws. Presently, the majority of traffic stops are conducted in a regimented and uniform manner as follows. First, the officer pulls his or her law enforcement vehicle up behind the identified motorist vehicle and initiates the lights of the law enforcement vehicle. This signals to the motorist that the officer wants to conduct a traffic stop. In response, the motorist will typically pull to the side of the road and stop his or her vehicle. The law enforcement vehicle will follow the motorist vehicle and stop behind it, leaving approximately a car length's distance between the two vehicles. Typically, the officer will position the law enforcement vehicle about two feet further toward the main roadway relative to the motorist vehicle so as to serve as a protective barrier to passing traffic.

As the vehicles are taking position on the side of the roadway as just described, the officer will communicate with his or her dispatch center via radio to provide the current location, the make/model of the motorist vehicle, and the license plate number of the motorist vehicle. During the majority of traffic stops, the officer will wait inside the law enforcement vehicle while the validity of the vehicle and license plate are verified. Each agency has a different standard operating procedure to obtain these verifications. If no issues with these identifiers arise, the officer will, in most circumstances, then exit the law enforcement vehicle and approach the stopped motorist vehicle on the driver's side thereof. During the initial contact with the motorist, the officer will request the motorists driver's license and registration documentation. The officer may also ask a series of questions related to the traffic infraction(s) that led to the stop. With documentation in hand, the officer will typically return to the law enforcement vehicle to further examine the validity of the documentation. If a citation or written warning is warranted, the officer will draft citation or written warning and return to the motorist vehicle to deliver it along with the motorist's documentation. At this time the motorist is typically free to leave.

Traffic stops are inherently dangerous for police officers, many of whom patrol and conduct stops alone. Officers typically take steps to protect themselves from passing traffic, such as using their own car as a barrier as described above, in addition, many states have enacted laws requiring freeway traffic approaching a stopped police vehicle to merge over to the left, leaving an entire lane as a buffer zone for the officer. Notwithstanding these efforts, according to FBI statistics, more officers are killed or injured annually during the course of traffic stops than at any other time, excluding vehicle accidents and affecting arrests.

SUMMARY OF THE INVENTION

In one embodiment, a system for assisting with vehicle traffic stops wherein a first vehicle stops a second vehicle is provided. The system includes a control system structured to be operative from within the first vehicle and an arm assembly structured to be coupled to the first vehicle. The arm assembly includes a telescoping arm member, a drive system, and a remote assembly coupled to a distal end of the arm member. The remote assembly includes a number of electronic devices for (i) collecting information at or from a location adjacent the remote assembly and providing the information to the control system and (ii) enabling two-way communication between the first vehicle and the location, wherein the arm member is structured to be selectively elongated and retracted by the drive system under control of the control system.

In another embodiment, a method of conducting a vehicle traffic stop is provided wherein a first vehicle stops a second vehicle. The method includes pulling the first vehicle behind the second vehicle, the first vehicle having an arm member coupled thereto and having a remote assembly coupled to a distal end of the arm member, elongating the arm member in a manner that positions the remote assembly adjacent a driver's side window of the second vehicle, collecting information at or from a location adjacent the remote assembly and providing the information to the first vehicle, and conducting two-way communications between the first vehicle and second vehicle using the remote assembly.

DETAILED DESCRIPTION OF EXEMPLARY EMBODIMENTS

Figure 1:
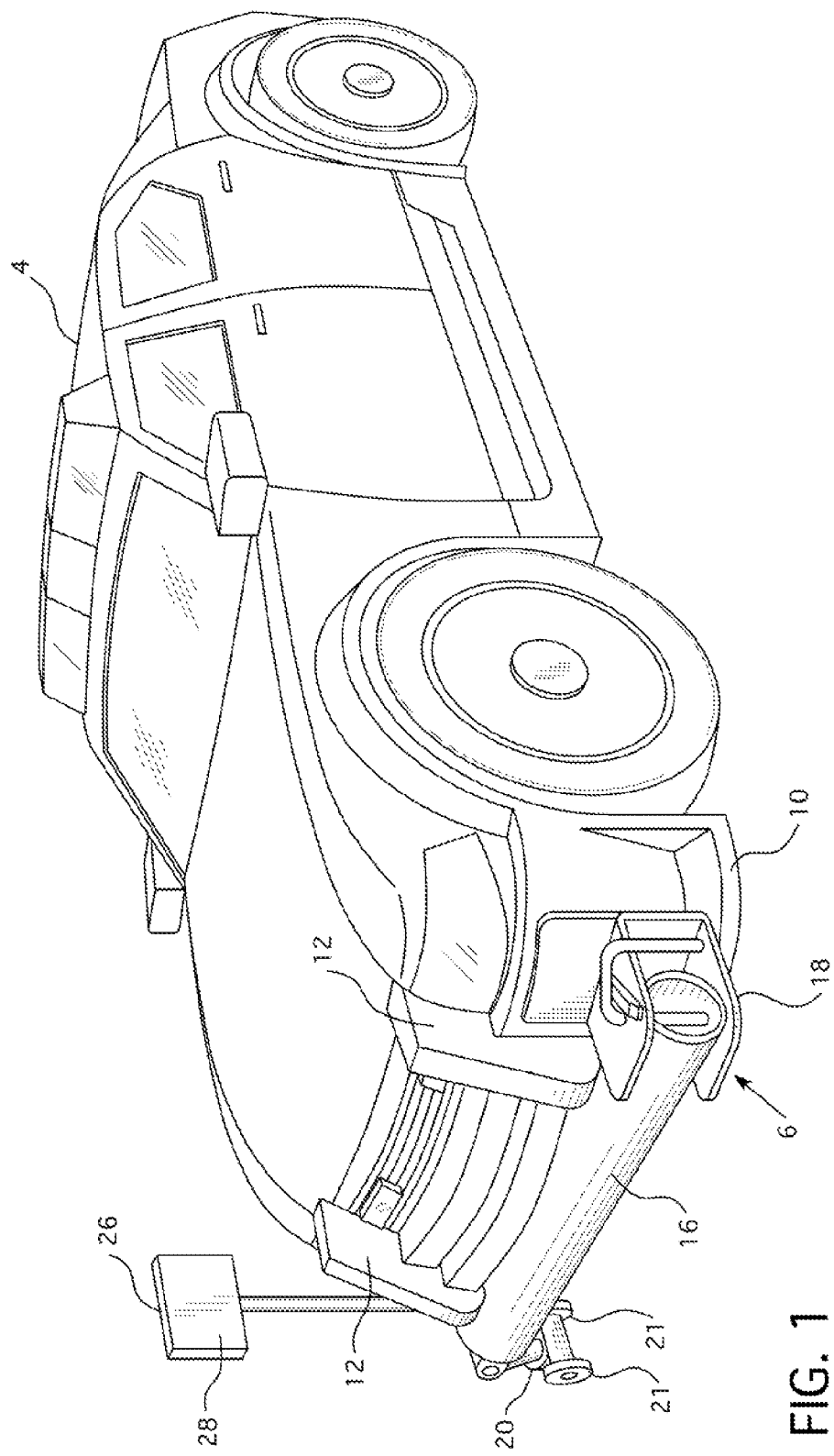
FIG. 1 is an isometric view and FIG. 2 is a front devotional view of a system for performing vehicle traffic stops according to a non-limiting exemplary embodiment of the disclosed concept.

As used herein, the singular form of "a", "an", and "the" include plural references unless the context clearly dictates otherwise.

As used herein, the statement that two or more parts or elements are "coupled" shall mean that the parts are joined or operate together either directly or indirectly, i.e., through one or more intermediate parts or elements, so long as a link occurs.

As used herein, "directly coupled" means that two elements are directly in contact with each other.

As used herein, "fixedly coupled" or "fixed" means that two elements are coupled so as to move as one while maintaining a constant orientation relative to each other.

As used herein, the "unitary" means a part is created as a single piece or unit. That is, a part that includes pieces that are created separately and then coupled together as a unit is not a "unitary" part or body.

As employed herein, the statement that two or more parts or elements "engage" one another shall mean that the parts exert a force against one another either directly or through one or more intermediate parts or elements.

As employed herein, the term "number" shall mean one or an integer greater than one (i.e., a plurality).

As employed herein, the term "video camera" shall mean a device structured for performing electronic motion picture acquisition.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As described in detail herein, the disclosed concept provides a system that serves as a facilitator for vehicle traffic stops by remotely gathering information, such as visual, audio, and or olfactory information from a stopped motorist vehicle and relaying that information back to the officer in the law enforcement vehicle for analysis. The system of the disclosed concept will eliminate the initial unknowns of traffic stops by allowing both the police officer and the motorist to remain in their respective vehicles. As described in detail herein, the system provides a mechanism for replacing the current preliminary face-to-face interface between officer and motorist by utilizing a remotely operated (by the officer from his or her vehicle) apparatus that will facilitate communication and gather vital information to assess the validity of the motorists legal right to remain on the roadway.

Figure 2:
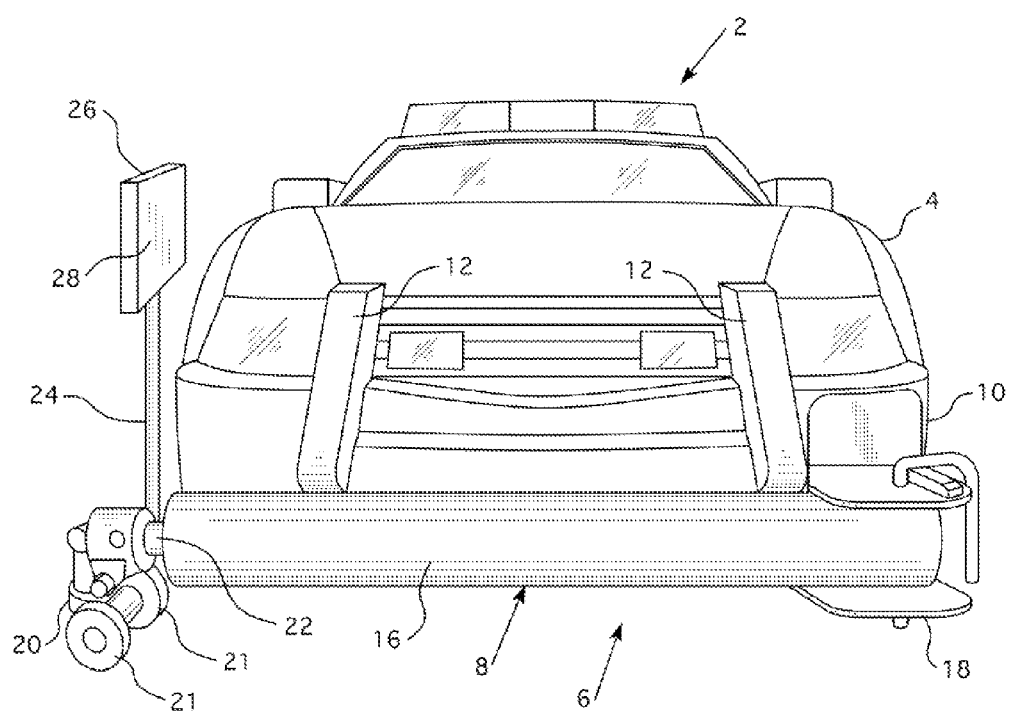

FIG. 1 is an isometric view and FIG. 2 is a front elevational view of a system 2 for performing vehicle traffic stops according to a non-limiting exemplary embodiment of the disclosed concept. As seen in FIGS. 1 and 2, system 2 includes a typical exemplary law enforcement vehicle 4 that is further equipped with a traffic stop enhancement system 6 according to the disclosed concept. As described in greater detail herein, traffic stop enhancement system 6 enables a police officer to remotely, from within law enforcement vehicle 4, gather information from a motorist vehicle during a traffic stop.

Traffic stop enhancement system 6 includes a folding and telescoping arm assembly 8 that is coupled to a front bumper 10 of law enforcement vehicle 4 below a push guard 12 of law enforcement vehicle 4. In addition, referring to FIG. 3, which is a block diagram of certain selected portions of traffic stop enhancement system 6, traffic stop enhancement system 6 further includes an in-vehicle control system 14 structured to enable a police officer to control traffic stop enhancement system 6 from within law enforcement vehicle 4. As described herein, arm assembly 8 is structured to be selectively deployed by a police officer from within law enforcement vehicle 4 during a traffic stop using control system 14 for purposes of gathering information from and/or providing information to the motorist during the traffic stop.

Figure 3:
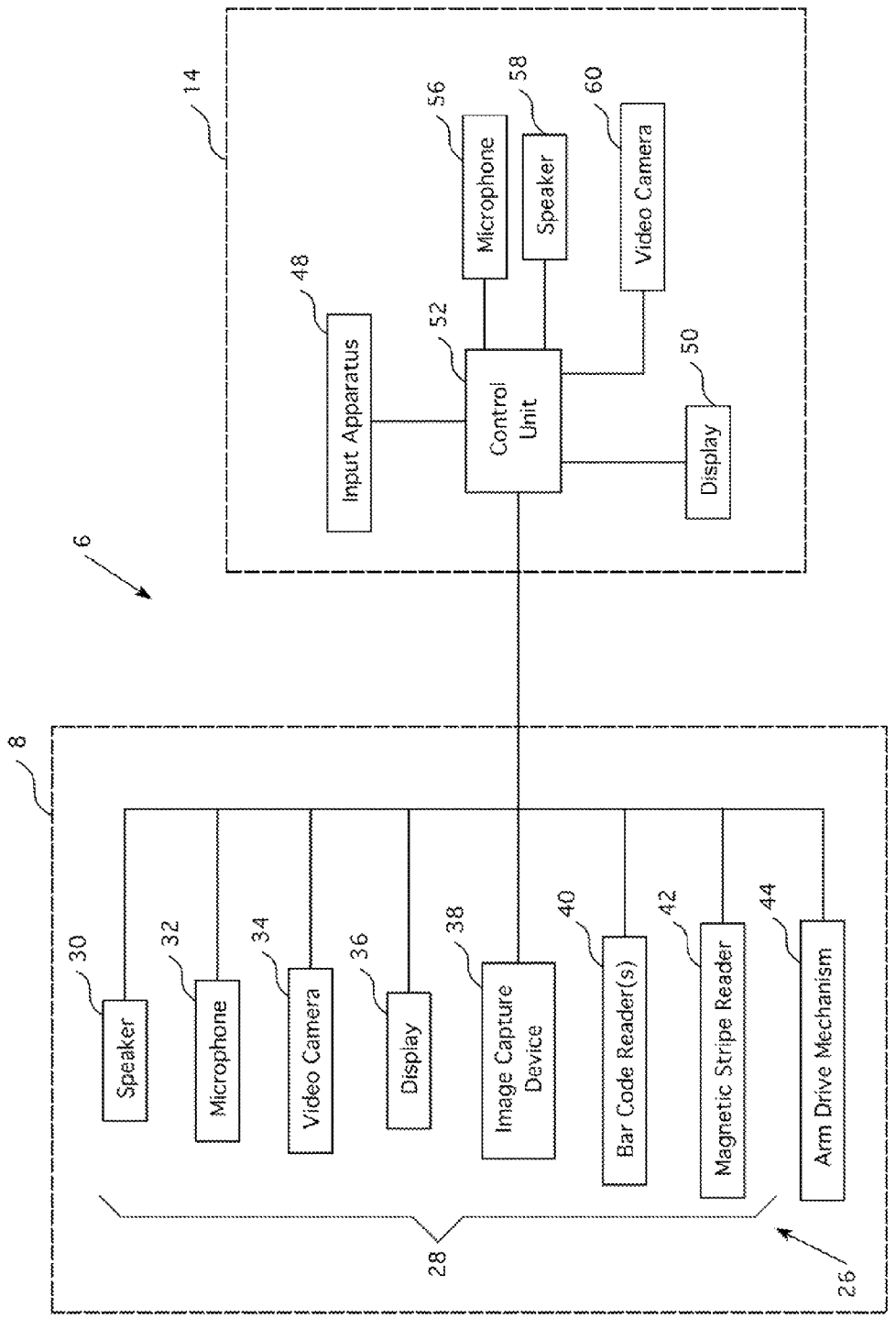
FIG. 3 is a block diagram showing certain selected portions of the traffic stop enhancement system of FIGS. 1 and 2.

Referring again to FIGS. 1 and 2, arm assembly 8 includes a telescoping arm member 16 that is coupled to front bumper 10 using a bracket assembly 18. Telescoping arm member 16 is structured to, under control of control system 14, be selectively elongated and retracted in a telescoping manner. The purpose of this telescoping functionality is described in detail elsewhere herein. Furthermore, a guide wheel assembly 20 including a pair of guide is wheels 21 is provided at the distal end 22 of arm member 16. Also provided at distal end 22 of arm member 16 is a post member 24 that carries a remote data collection and communications assembly 26. As described in greater detail herein, remote data collection and communications assembly 26 includes a number of electronic information devices 28 for gathering information from and/or providing/communicating information to a motorist during a traffic stop. Referring to FIG. 3, in one basic, non-limiting exemplary embodiment of the disclosed concept, the electronic information devices 28 provided as part of remote data collection and communications assembly 26 include a speaker 30 for communicating audio information to a motorist (generated from within law enforcement vehicle 4 as described herein), a microphone 32 for collecting audio information from a motorist, a video camera 34 for collecting video images from a motorist and/or from within the motorist's vehicle, a display 36, such as a liquid crystal display, for providing video images to a motorist (generated from within law enforcement vehicle 4 as described herein), an image capture device 38, such as digital camera, for capturing images of certain items as described herein, a number of barcode readers 40, such as a 1D and/or a 2D barcode reader, for capturing barcode information as described herein, and a magnetic stripe reader 42 for capturing magnetic stripe information as described herein.

Figure 4:
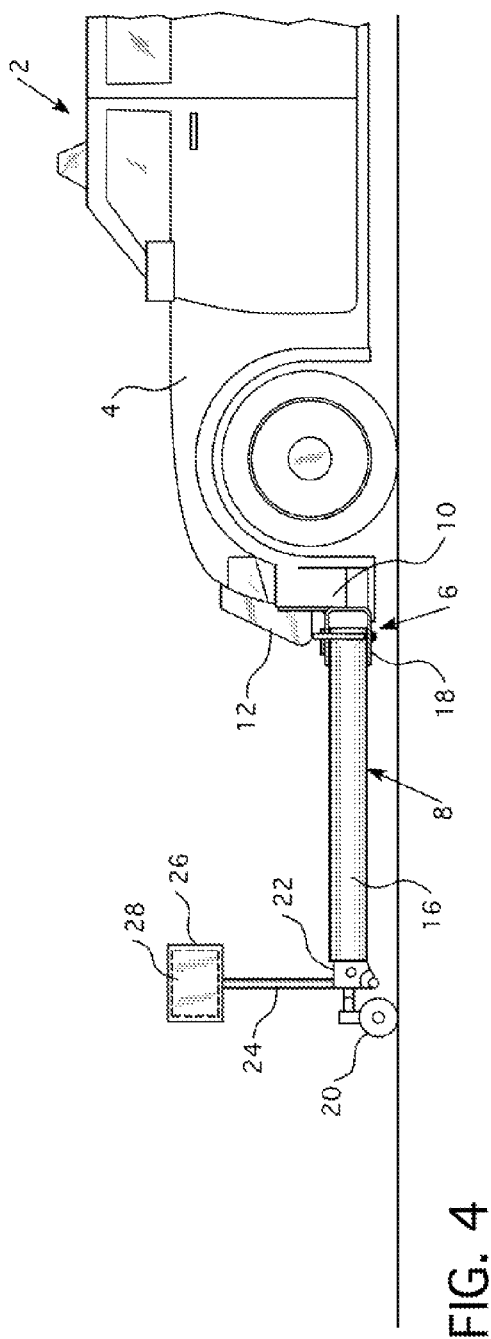
FIGS. 4, 5 and 6 are various views illustrating deployment of the traffic stop enhancement system of FIGS. 1 and 2.
Figure 6:
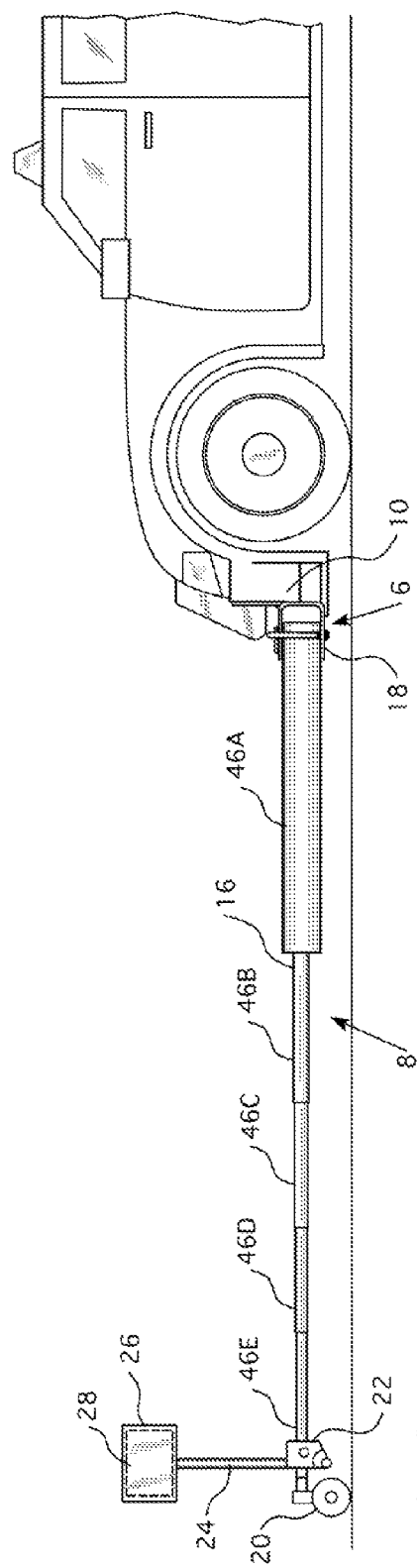
Figure 5:
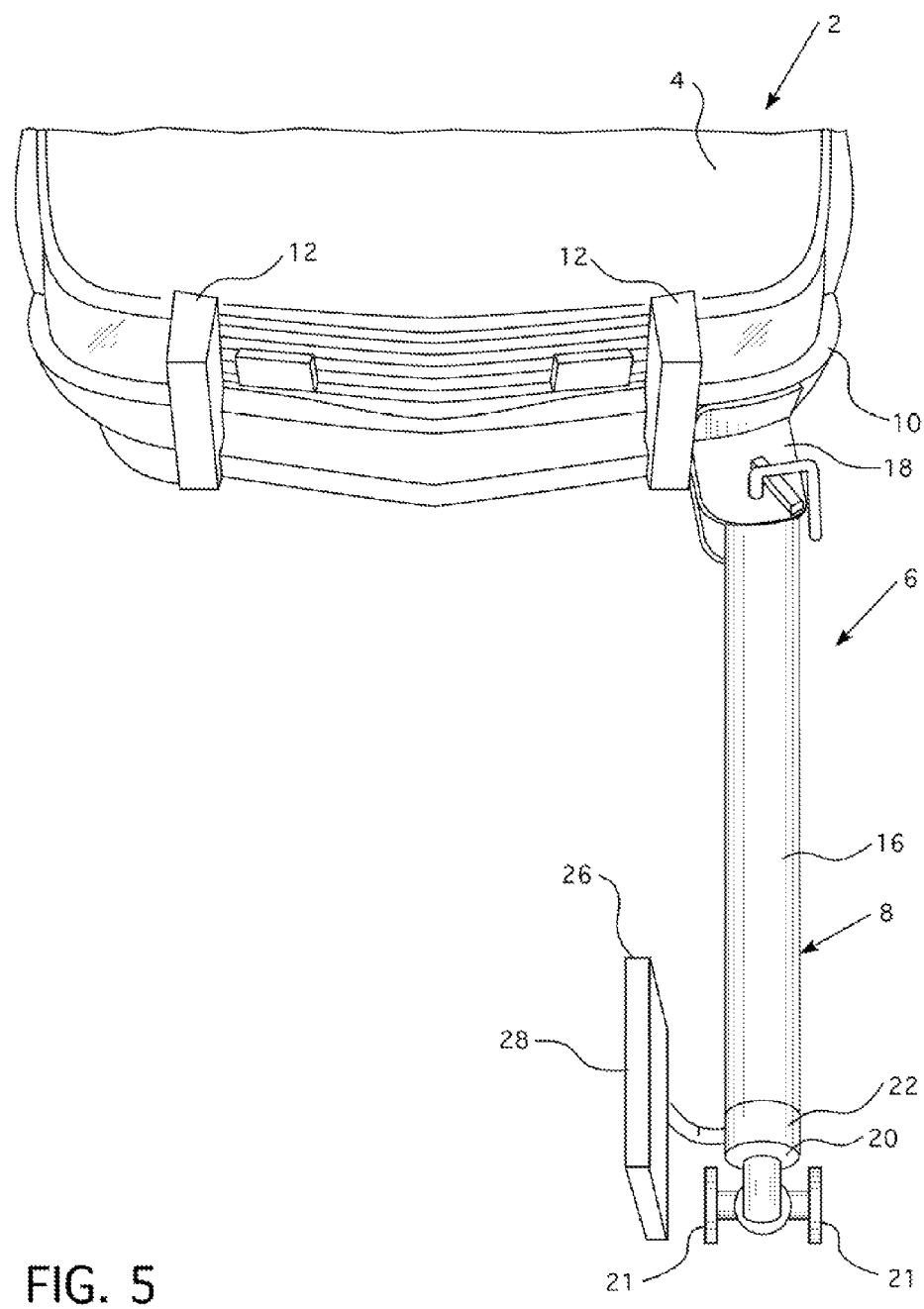

Referring to FIG. 3, arm assembly 8 further includes an arm drive mechanism 44 that, under the control of control system 14, controls the movement of arm assembly 8 as described herein. In the exemplary embodiment, arm assembly 8 is structured for movement in two manners. First, arm assembly 8 is selectively movable in a folding manner away from and back toward front bumper 10. In particular, arm assembly 8 is movable from a first, non-deployed position as shown in FIG. 1 wherein it is substantially parallel to front bumper 10, to a second, intermediately deployed position as shown in FIGS. 4 and 5, wherein it is substantially perpendicular to front bumper 10. Second, arm assembly 8 is also selectively movable in a telescoping manner such that it can be selectively extended and retracted as desired. In particular, arm assembly 8 is movable from a retracted position as shown in FIGS. 4 and 5 to a fully deployed, elongated position as shown in FIG. 6. For this purpose, as seen in FIG. 6, arm member 16 includes a plurality of arm portions or segments 46 (labeled 46A-46E) that are able to be nested within one another and extended relative to one another to perform the telescoping function. The significance of being able to move arm assembly 8 from the non-deployed position to the fully deployed position in connection with the performance of a vehicle traffic stop is described elsewhere herein.

Arm drive mechanism 44 may be any of a number of known or hereafter developed drive mechanisms that are structured to enable the selective movement of arm assembly 8 under the control of control system 14 as just described. For example, and without limitation, arm drive mechanism 44 may include a number of pneumatic drives which are structured to independently provide the folding and telescoping movement of arm assembly as described above. Still other types of arm drive mechanisms, non-limiting examples of which are described elsewhere herein, may also be employed within the scope of the disclosed concept.

Referring again to FIG. 3, certain selected elements of control system 14 according to the exemplary embodiment will now be described. As noted elsewhere herein, the elements of control system 14 are housed and provided within law enforcement vehicle 4 so as to be accessible by a police officer while sitting therein, and are operatively coupled to the eras of arm assembly 8. As seen in FIG. 3, the exemplary control system 14 includes an input apparatus 48, such as a keypad or touchscreen, a display 50, such as an LCD, and a control unit 52. A police officer is able to provide input into control unit 52 using input apparatus 48, and control unit 52 provides output signals to display 50 to enable display 58 to display information to the police officer as described in detail herein. Control unit 52 is operatively coupled to each of the elements of arm assembly 8 shown in FIG. 3 and comprises a processor and a memory. The processor may be, for example and without limitation, a microprocessor (μP), a microcontroller, or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The memory has stored therein a number of routines that are executable by the processor to enable operation and control of arm assembly 8 as described herein. In addition, control system 14 includes a microphone 54 structured to enable a police officer to provide audio that is output by remote data collection and communications assembly 26, a speaker 58 that is structured to communicate audio to the police officer that is collected by remote data collection and communications assembly 26 (by microphone 32), and a video camera 60 that is structured to capture video of the police officer for output by remote data collection and communications assembly 26 (by display 36).

Operation of traffic stop enhancement system 6 during a typical vehicle traffic stop will now be described. First, after the motorist pulls the motorist vehicle off the roadway in response to the lights of law enforcement vehicle 4, the police officer will pull law enforcement vehicle 4 up behind the motorist vehicle, leaving about a car's length between the two vehicles. The police officer will then, from within law enforcement vehicle 4 and using input apparatus 48 of control system 14, deploy arm assembly 8, in particular, the officer will provide inputs to control unit 52 (via input apparatus 48) which in turn will cause control unit 52 to control arm drive mechanism 44 to cause arm assembly 8 to fold out as shown in FIGS. 4 and 5. As a result, arm member 16 will extend from front bumper 10 and will be positioned in a forward manner slightly left of the rear bumper of the motorist vehicle. While the officer remains in law enforcement vehicle 4, the officer will provide further inputs to control unit 52 which in turn will cause control unit 52 to control arm drive mechanism 44 to cause arm member 16 to elongate outwardly as shown in FIG. 6 towards the driver's side window of the motorist's vehicle. The positioning of arm member 16 in this manner serves two purposes. First, it transports remote data collection and communications assembly 26 to the driver's side window so that it is in a position to gather and/or communicate information. In the exemplary embodiment, remote data collection and communications assembly 26 will include an additional drive mechanism (not shown), such as an electric motor, that is controllable by control system 14 (e.g., by a portion of input apparatus 48) that allows remote data collection and communications assembly 26 to be selectively moved to be in an optimal position for data collection and/or communication. Second, the positioning of arm member 16 acts as a barricade to the driver's side front and rear doors, preventing the motorist from opening and exiting the vehicle.

Next, through cooperative use and operation of speaker 30, microphone 32, video camera 34, display 50, microphone 56, speaker 58, and video camera 60, the police officer will be able to visually inspect the motorist and the interior of the motorist vehicle (within the plain view doctrine parameters) and communicate with the motorist (including 2-way audio and video), all without leaving the confines of law enforcement vehicle 4. In addition, in a typical vehicle traffic stop, the motorist will be instructed to provide his or her license and registration, which will both be electronically scanned by remote data collection and communications assembly 26 so that the information contained therein can be provided to the police officer for scrutiny. In particular, the motorist will be instructed to position his or her license and registration so that image capture device 38 can capture one or more images thereof, which images are transmitted to control unit 14 for display on display 50. The motorist will also be instructed to utilize barcode reader(s) 40 to read one or more barcodes from those items and utilize magnetic stripe reader 42 to read one or more magnetic stripes on those items, if present. The information which is read will be transmitted to control unit 14 for display on display 50. At this point, the police officer, without leaving law enforcement vehicle 4, will have all of the information that is needed to determine whether a citation or written warning is warranted. In the exemplary embodiment, if it is determined that a citation or written warning is warranted, the motorist will be advised by audio signal that the citation or written warning will be mailed to him or her for payment and/or review. At this time, the motor vehicle stop has concluded and the motorist is free to leave.

If at any time during the vehicle traffic stop the officer instructs the motorist to exit the motorist vehicle, arm member 16 can be remotely retracted from within law enforcement vehicle 4 to allow for this action.

Figure 7:
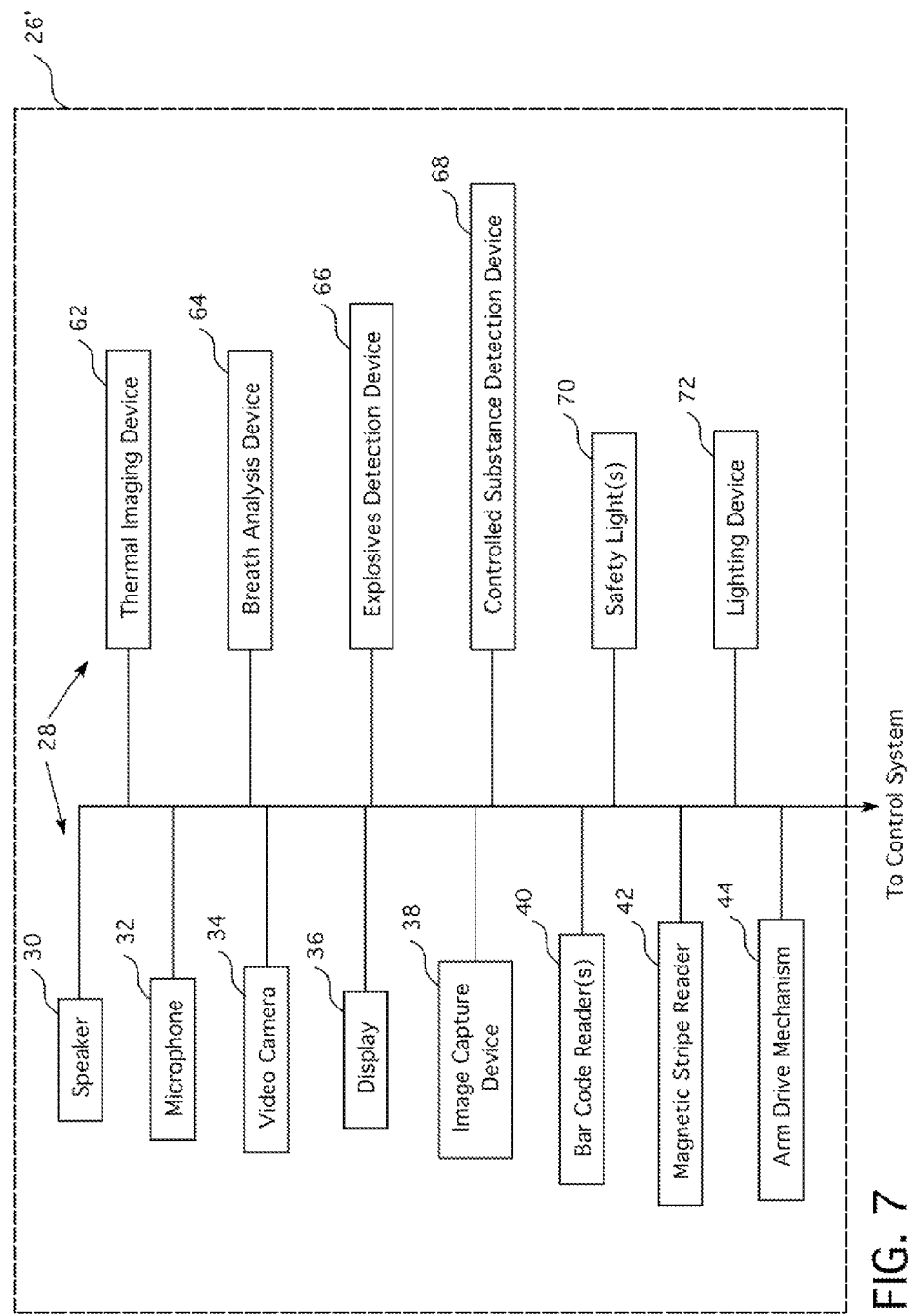
FIG. 7 is a schematic diagram of a remote data collection and communications assembly according to an alternative exemplary embodiment of the disclosed concept.

In the exemplary embodiment of traffic stop enhancement system 6 described above, remote data collection and communications assembly 26 is described as including a particular group of exemplary electronic data devices 28. It will be understood, however, that the enumerated devices are meant to be exemplary only, and that such devices may include additional devices in addition to or instead of the enumerated devices. FIG. 7 is a schematic diagram of a remote data collection and communications assembly 26' according to an alternative exemplary embodiment. Remote data collection and communications assembly 26' includes many of the same elements and components as remote data collection and communications assembly 26, and like elements are labeled with like reference numerals. However, remote data collection and communications assembly 26' includes a number of additional electronic data devices 28 that may be used in any combination or subset (for example, with one or more of the devices shown in FIG. 3) to form a particular implementation. In the illustrated embodiment, the additional electronic data devices 28 are operatively coupled to control system 14 and include a thermal imaging device 62, such as a thermal imaging camera, which may be used to detect the number of occupants in a stopped motorist vehicle, a breath analysis device (e.g., a Breathalyzer® device) 64 for estimating blood alcohol content (BAC) from a breath sample taken form the motorist, an explosives detection device 66 for detecting trace signatures for various explosive materials, such as detection devices that are based on mass spectrometry and gas chromatography, a controlled substance detection device 68 for detecting trace signatures for various controlled substances, such as detection devices that are based on mass spectrometry and gas chromatography, a number of safety lights 70, such as, without limitation, red and blue and/or yellow LED lights, and a lighting device 72, such as a spotlight or strobe.

Figure 8:
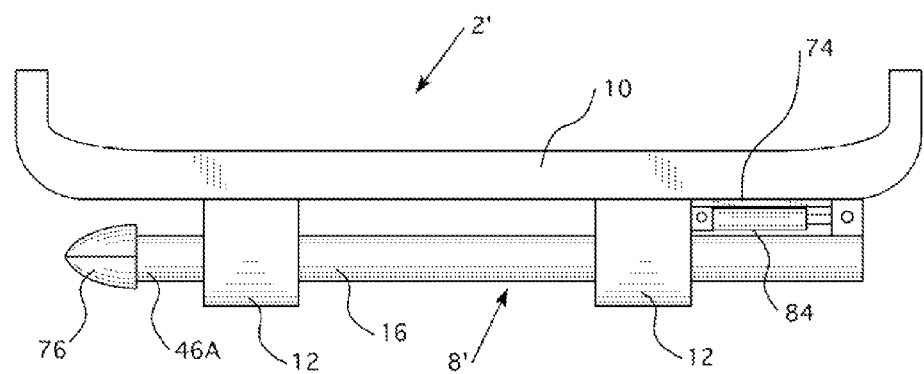
FIG. 8 is a schematic top plan view.
Figure 9:
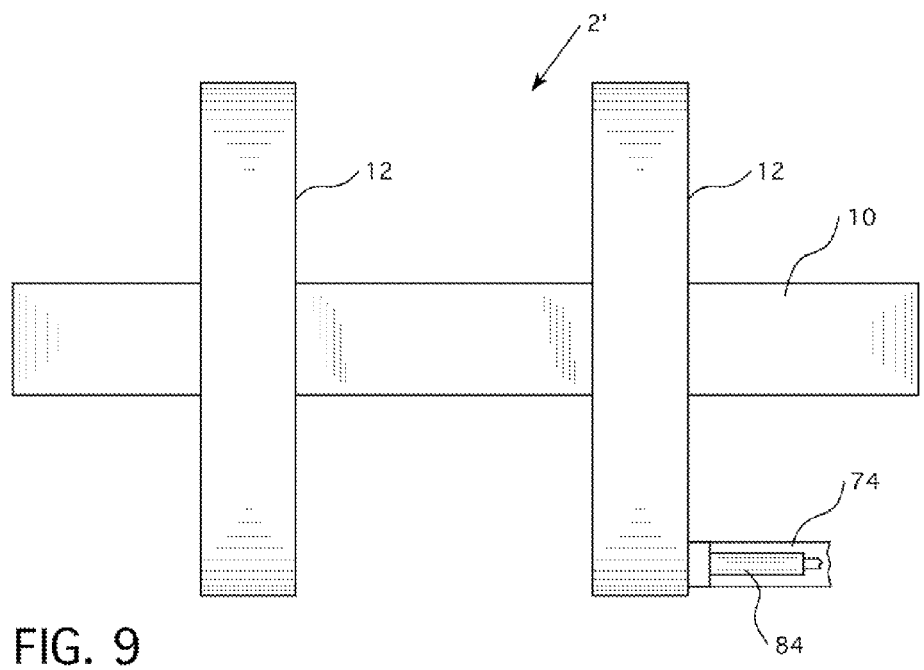
FIG. 9 is a schematic front elevational view.
Figure 10:
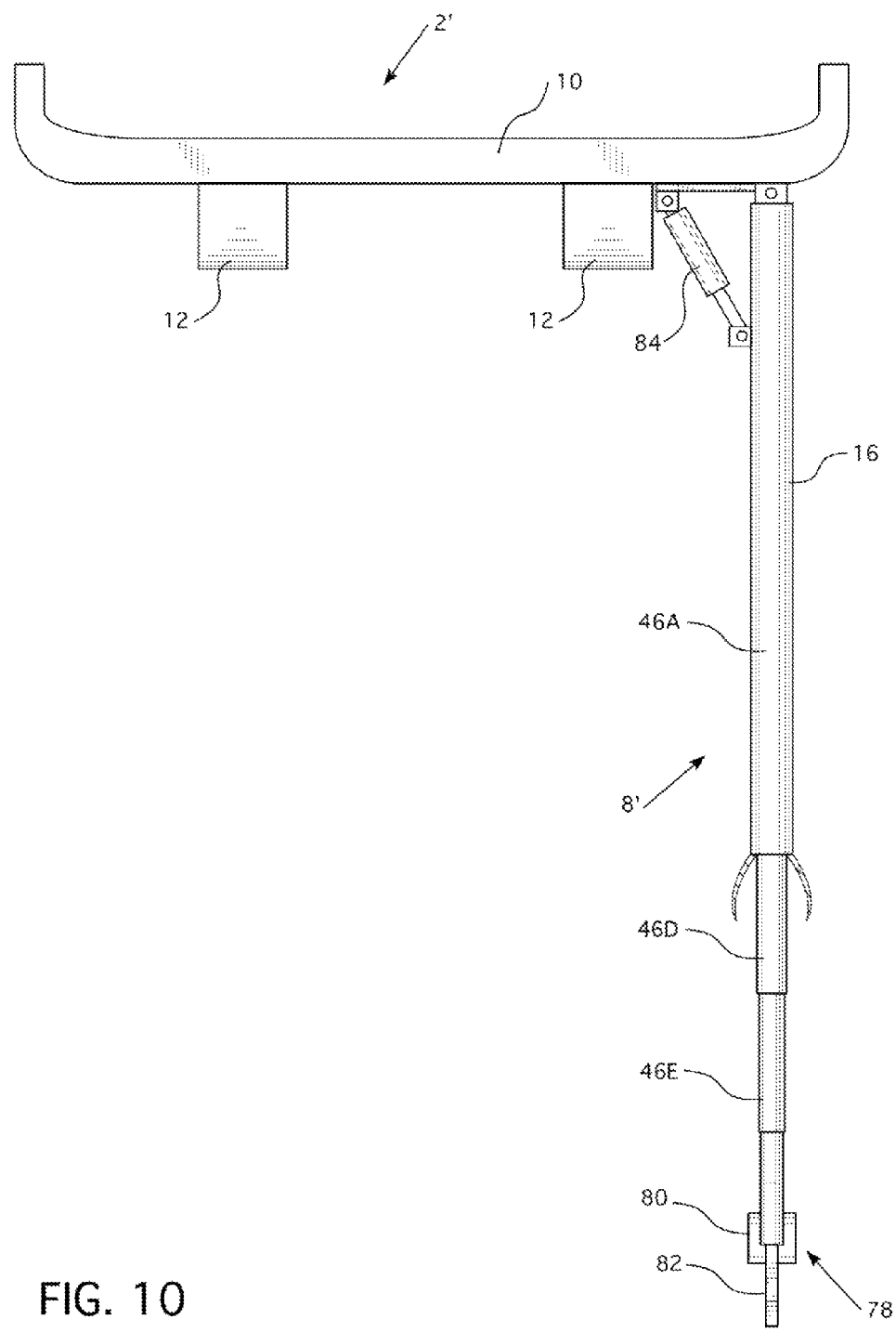
FIG. 10 is a schematic top plan view of an arm assembly according to an alternative exemplary embodiment of the disclosed concept.
Figure 11:
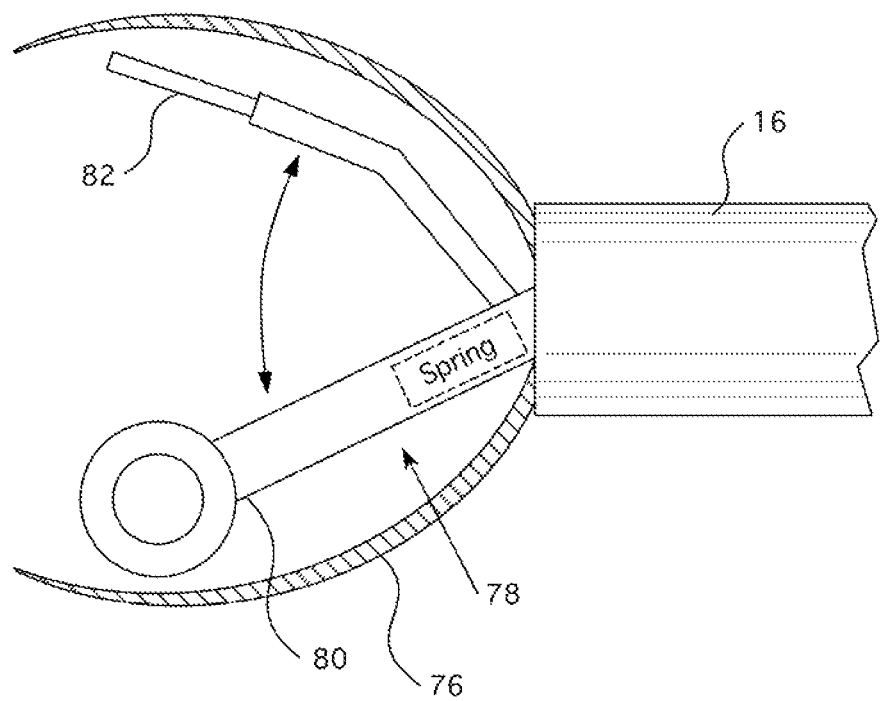
FIG. 11 is a schematic diagram of a wheel and remote data collection and communications assembly according to an alternative exemplary embodiment of the disclosed concept.

FIGS. 8-11 are schematic diagrams showing various portions of art alternative system 2' for performing vehicle traffic stops according to an alternative non-limiting exemplary embodiment of the disclosed concept. System' includes a number of the same elements as system 2, and like elements are labeled with like reference numerals. System 2' includes an alternative arm assembly 8' that is coupled to push guard 12 of law enforcement vehicle 4 using a mounting bracket 74. In the exemplary embodiment, as seen in FIG. 8, push guard extends out past the alternative arm assembly 8' when the alternative arm assembly 8' is not deployed. As seen in FIG. 8, alternative arm assembly 8' includes arm member 16 that has been modified to include a bell housing member 76 that is provided at the distal end of a portion 46A arm member 16. Bell housing 76 is a member made of, for example, and without limitation, a flexible material such as rubber or silicone that is structured to be biased into a closed position as shown in FIG. 8. The purpose of bell housing member 76 is to protect alternative wheel and remote data collection and communications assembly 78 (FIG. 11) when not in use. As seen in FIG. 11, alternative wheel and remote data collection and communications assembly 78 includes a wheel assembly 80 that is similar to wheel assembly 20, and a remote data collection and communications assembly 82 that is similar to remote data collection and communications assembly 26 (and includes similar parts). However, in remote data collection and communications assembly 78, wheel assembly 80 and remote data collection and communications assembly 82 are spring biased outwardly from one another as shown by the arrows in FIG. 11. The significance of this feature is described below. In addition, as seen in FIGS. 9 and 10, alternative arm assembly 8' includes a pneumatic drive mechanism 84 (forming part of arm drive mechanism 44) for pivoting modified arm member 16 away from front bumper 10 under control of control system 14.

In operation, when it is desired to deploy alternative arm assembly 8', modified arm member 16 is first pivoted away from front bumper 10 to a position as shown in FIG. 10. Then, by operation of arm drive mechanism 44, arm member 16 is caused to elongate. When this is done, bell housing 76 is caused to open i.e., it is pushed open) and wheel assembly 80 and remote data collection and communications assembly 82 are caused to move away from one another as shown in FIG. 11 by operation of the spring assembly thereof. When fully elongated, alternative arm assembly 8' will be deployed in a manner similar to that shown in FIG. 6, and remote data collection and communications assembly 82 will able to provide the same functionality as remote data collection and communications assembly 26 as described herein.

Figure 15:
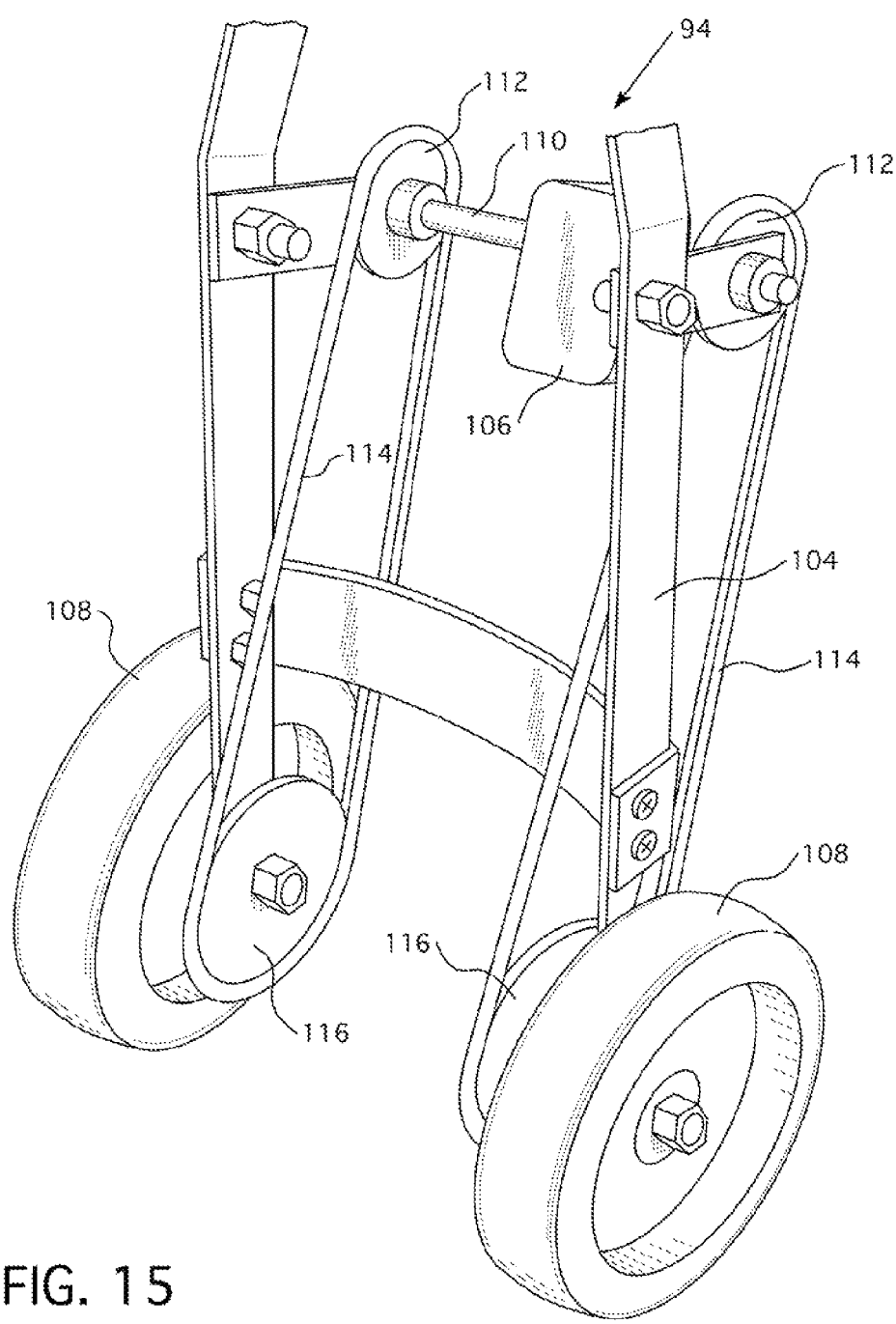
FIG. 15 is an isometric view of the drive wheel assembly of FIGS. 12 and 13.
Figure 16:
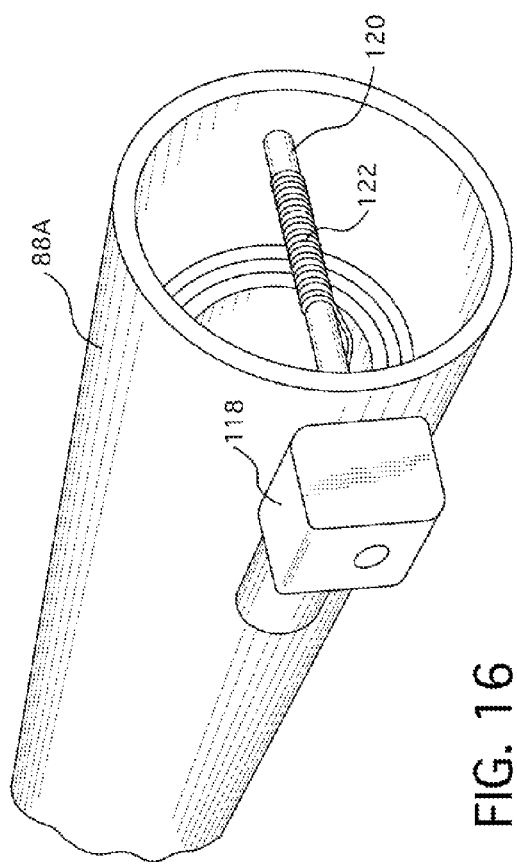
FIG. 16 is a rear view of the alternative arm assembly of FIG. 12.
Figure 17:
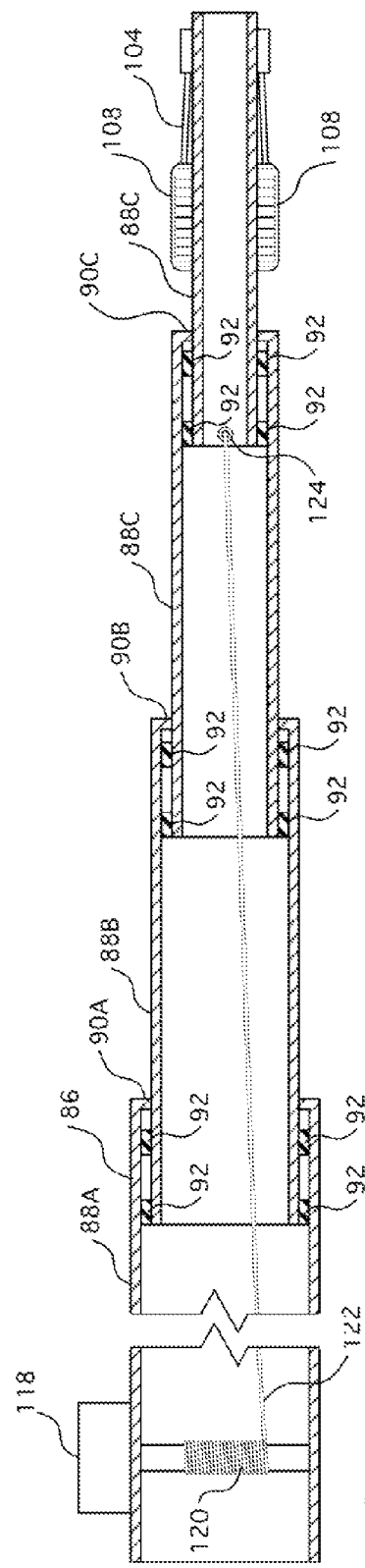
FIG. 17 is a cross sectional view of the alternative arm assembly of FIG. 12.

FIGS. 12-17 are schematic diagrams showing various portions of another alternative arm assembly 8" that may be coupled to push guard 12 of law enforcement vehicle 4 to form another alternative version of system 2 for performing vehicle traffic stops according to another alternative non-limiting exemplary embodiment of the disclosed concept. Arm assembly 8" includes a number of the same elements as arm assembly 8, and like elements are labeled with like reference numerals. Arm assembly 8" includes telescoping arm member 86 (similar to arm member 16) that includes a plurality of (e.g., four) arm portions or segments 88 (labeled 88A-88D; FIG. 17) that are able to be nested within one another and extended relative to one another to perform the telescoping function described herein. As seen in FIG. 17, segment 80A includes a retaining ring 90A at the distal end thereof, segment 88B includes a retaining ring 90B at the distal end thereof and a number of retaining rings 92 provided on the outside of the proximal end thereof, segment 88C includes a retaining ring 90C at the distal end thereof and a number of retaining rings 92 provided on the outside of the proximal end thereof, and segment 80D includes a number of retaining rings 92 provided on the outside of the proximal end thereof. Retaining rings 90 and 92 of each respective segment 80 function together to provide a abutting stops during extension of arm member 86 as described herein. In the exemplary embodiment, retaining rings 90 and 92 may be made of PVC, Teflon®, Delrin®, nylon, or any other suitable material. In the exemplary embodiment, segment 80A is a 4 inch PVC schedule 80 pipe 75 inches long), segment 80B is a 3 inch PVC schedule 80 pipe, segment 80C is a 2.5 inch PVC schedule 80 pipe, and segment 80D is a 2 inch PVC schedule 80 pipe.

Figure 12:
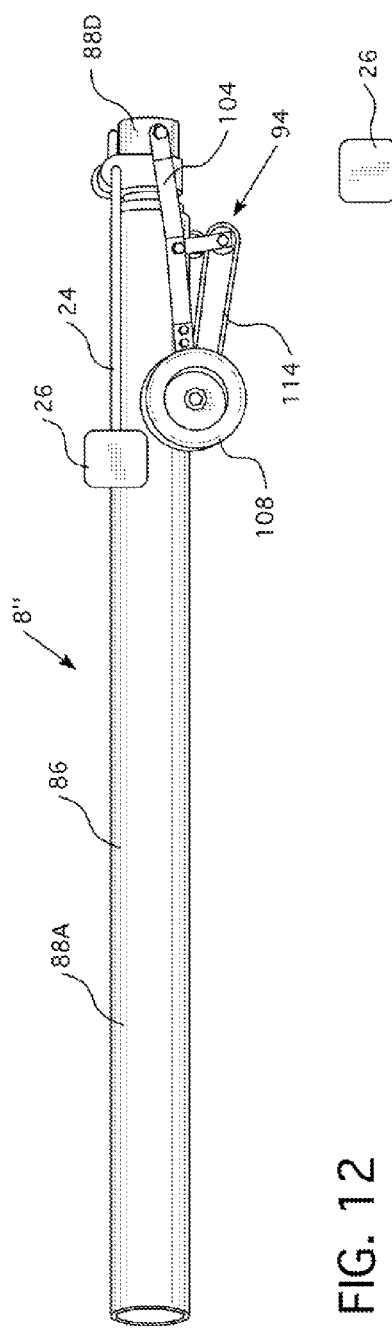
FIG. 12 is a side view of an alternative arm assembly having an alternative drive wheel assembly (in a retracted condition) that may be employed in a system for performing vehicle traffic stops according to another alternative ion-limiting exemplary embodiment of the disclosed concept.
Figure 13:
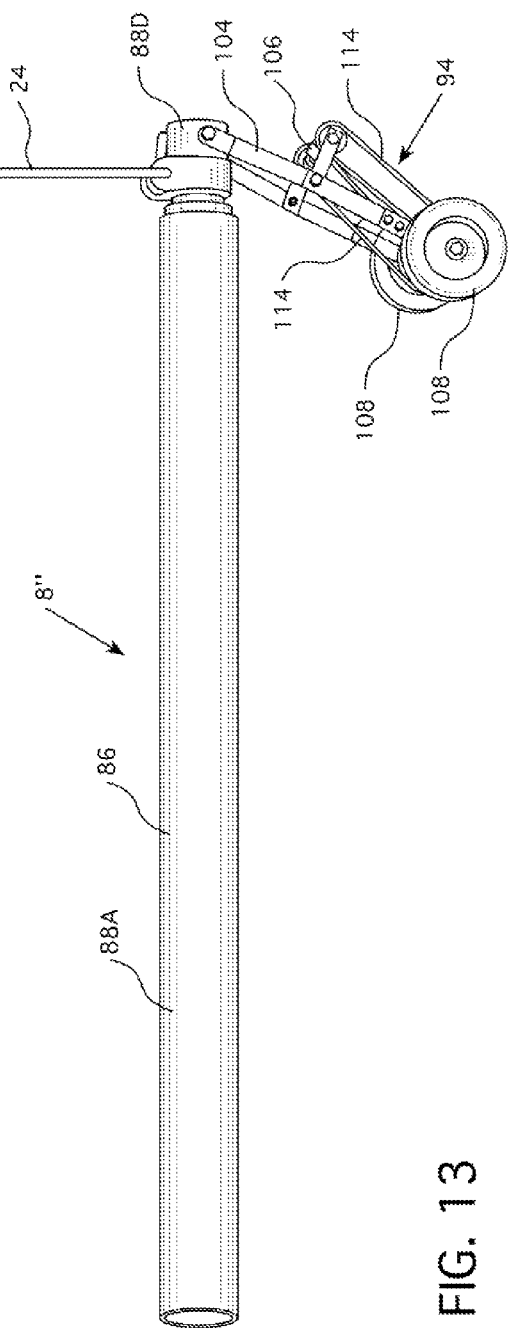
FIG. 13 is a side view of the alternative arm assembly of FIG. 12 showing the drive wheel assembly in an extended condition.
Figure 14:
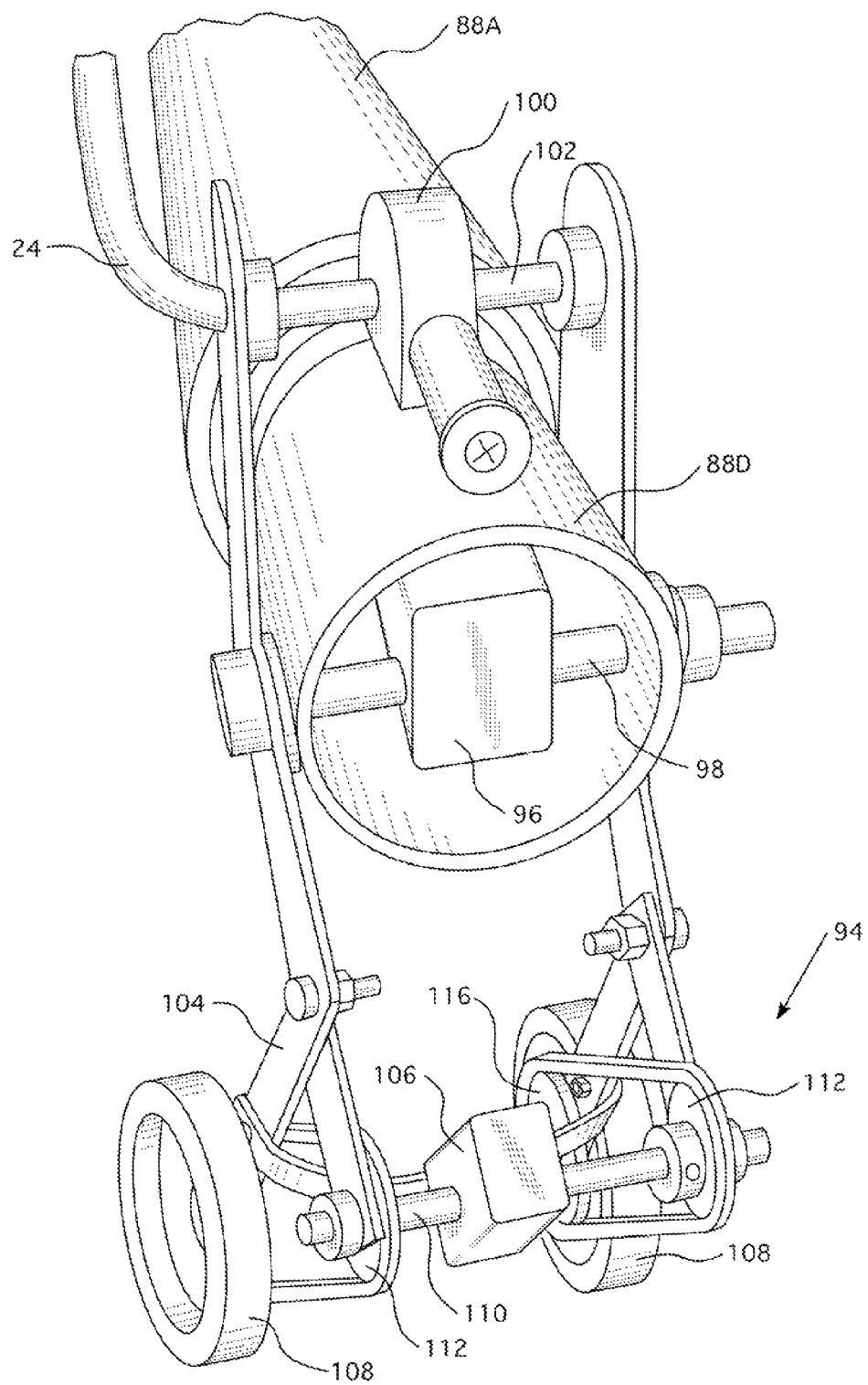
FIG. 14 is a front view of the alternative arm assembly of FIG. 12 showing the drive wheel assembly in an extended condition.

Referring again to FIGS. 12 and 13, arm assembly 8" includes a drive wheel assembly 94 that is movably coupled to the distal end of segment 88D. Arm assembly 8" also includes post member 24 as described herein that carries remote data collection and communications assembly 26 as described herein. FIG. 12 shows the drive wheel assembly 94 and the post member 24 and remote data collection and communications assembly 26 in a retracted position, and FIG. 13 shows the drive wheel assembly 94 and the post member 24 and remote data collection and communications assembly 26 in an extended position (the position which it would be used during a traffic stop). Referring to FIG. 14, which is a front isometric view of arm assembly 8", arm assembly 8" includes a motor 96 (e.g., a 12 V gear motor) coupled to a shaft 98. Motor 96 and shaft 98 are provided within the interior of the distal end of segment 88D. Shaft 98 is operatively coupled to drive wheel assembly 94. Motor 96 and shaft 98 function to selectively extend and retract drive wheel assembly 94 under control of control system 14. Arm assembly 8" further includes a motor 100 coupled to shaft 102. Motor 100 and shaft 102 are provided on the exterior of the distal end of segment 88D. Shaft 102 is operatively coupled to post member 24. Motor 100 and shaft 102 function to selectively extend and retract post member 24 and data collection and communications assembly 26 under control of control system 14.

As described in greater detail herein, drive wheel assembly 94 is provided to enable the selective extension of arm member 86 under control of control system 14. Referring to FIG. 15, which is an isometric view of drive wheel assembly 94, drive wheel assembly 94 includes a framework 104 and supports a motor 106 (e.g., a 12 V reversible gear motor) and a pair of wheels 108. Motor 106 is coupled to a shaft 110 having chain sprockets 112 located at opposite ends thereof. The chain sprockets 112 are coupled to chains 114, which in turn are coupled to sprockets 116. Each sprockets 116 is coupled to a shaft of a respective one of the wheels 108. As will be appreciated, as motor 106 turns shaft 110, the rotation of chain sprockets 112 is coupled to chain sprockets 116 by chains 114 so as to rotate wheels 108. In an alternate embodiment, wheels 108 may be replaced by track members that are similarly driven by motor 106.

Referring to FIGS. 16 and 17, the proximal end of segment 88A includes a motor 118 coupled to the outside of segment 88A. Motor 118 is coupled to and drives a shaft 120 under control of control system 14. A cable 122 (e.g., a ⅙ or ⅛ inch stainless steel aircraft grade cable) has a first end coupled to shaft 120 and a second end coupled to the proximal end of segment 88D by an appropriate coupling member 124, such as a ring. Motor 118 and cable 122 are utilized to retract arm assembly 8" under control of control system 14.

In operation, when it is desired to deploy arm assembly 8", arm member 86 is first pivoted away from front bumper 10 as described herein (e.g., by pneumatic drive mechanism 84) to a position similar to that shown in FIG. 10. Next, motor 96 and motor 100 are each driven to extend drive wheel assembly 94 and post member 24 and data collection and communications assembly 26, respectively, to the position shown in FIG. 13. Then, motor 118 is driven to move wheels 108 as described herein to elongate arm member 86. When fully elongated, arm assembly 8" will be deployed in a manner similar to that shown in FIG. 6, and the traffic stop may proceed as described elsewhere herein. When the traffic stop is completed, motor 96 and motor 100 are each driven to retract drive wheel assembly 94 and post member 24 and data collection and communications assembly 26, respectively. Then, motor 118 is driven to retract arm member 86 to the position shown in FIG. 12. Thereafter, arm member 86 is pivoted back toward front bumper 10 so that law enforcement vehicle 4 will then be in a condition to drive away.

Figure 18:
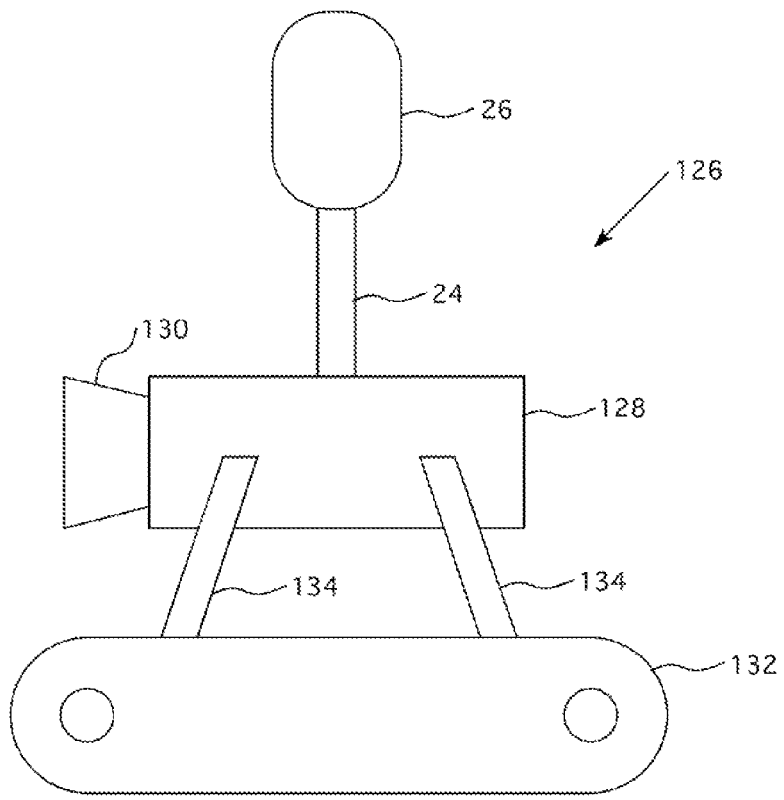
FIG. 18 is a schematic diagram of a remotely operated vehicle that may be employed in connection with an alternative embodiment of the disclosed concept.
Figure 19:
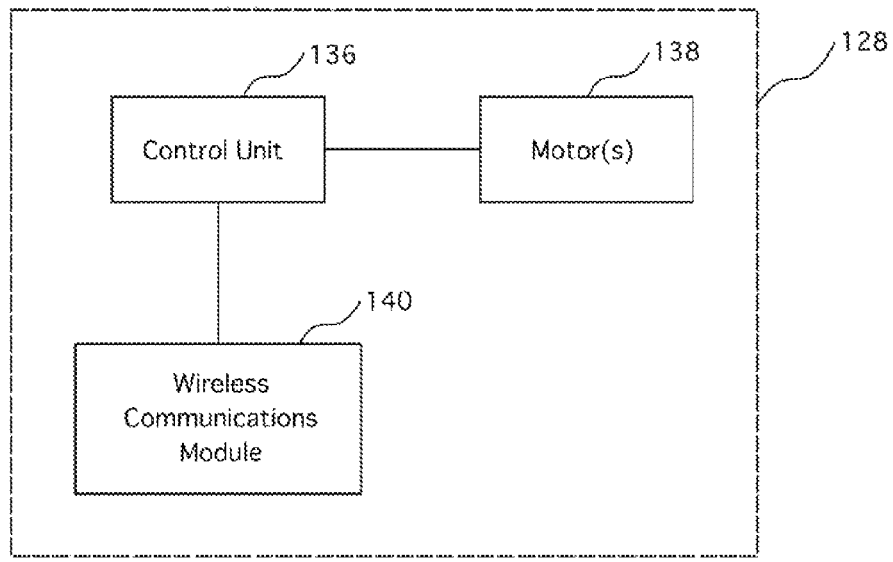
FIG. 19 is a lock diagram showing portion of the remotely operated vehicle of FIG. 18.

In still a further alternative embodiment, drive wheel assembly 94 and post member 24 and data collection and communications assembly 26 of FIGS. 12-17 may be replaced by a remotely operated vehicle (ROV) 126 as shown in FIG. 18. ROV 126 is structured to be controlled by control system 14, and is separable from and selectively dockable to the distal end of arm member 86. ROV 126 includes a main housing 128, and a docking funnel/port 130 coupled to main housing 128 that is structured to enable selective docking of ROV 126 to the distal end of arm member 86. ROV 126 also includes post member 24 that carries a remote data collection and communications assembly 26 as described elsewhere herein. In the exemplary embodiment, post member 24 is a selectively retractable folding member. ROV 126 also includes a drive assembly 132 that is coupled to main housing 128 by selectively foldable/extendable support legs 134. Drive assembly 132 may include a track member as shown, or, alternatively, a pair of wheels similar to wheels 108. As shown in FIG. 19, main housing 128 houses a control unit 136, which lay be similar in structure to control unit 52 described elsewhere herein, a number of motors 138 coupled to post member 24, support legs 134 and drive assembly 132 to selectively drive those components, and a wireless communications module 140 structured to enable wireless communications with control unit 14 of law enforcement vehicle 4. In this embodiment, drive assembly 132, driven by a motor 138, is the mechanism which is used to extend arm member 86 under control of control unit 14 during vehicle stop. In addition, in this embodiment, control unit 14 may cause ROV 126 to be separated from arm member 86 when arm member 86 is fully extended to enable ROV 126 to be selectively moved around the stopped vehicle using drive asset ably 132 in order to collect data and/or communicate using data collection and communications assembly 26 as described herein. Thus, this embodiment provides added flexibility by enabling data collection and/or communications to occur at various locations separate from the distal end of arm member 86. When the traffic stop is completed, ROV 126 may be re-docked with the distal end of arm member 86 using docking funnel/port 130, and arm member 86 may be retracted using motor 118 and cable 122 as described herein. In addition, in the exemplary embodiment, before such retraction is performed, post member 24 and support legs 134 will be retracted by a motor 138 under control of control system 14.

Thus, as described in detail above, the disclosed concept provides various embodiments of a system that serves as a facilitator for vehicle traffic stops that will allow a police officer to remotely gather information and to communicate with a motorist without leaving the law enforcement vehicle. The disclosed concept also provides a mechanism that acts as a barricade, preventing a motorist from exiting his or her vehicle.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such element. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for assisting with vehicle traffic stops wherein a first vehicle stops a second vehicle, comprising:
   a control system structured to be operative from within the first vehicle; and
   an arm assembly structured to be coupled to the first vehicle, the arm assembly including:
   a telescoping arm member;
   a drive system; and
   a remote assembly coupled to a distal end of the arm member, the remote assembly including a number of electronic devices for (i) collecting information at or from a location adjacent the remote assembly and providing the information to the control system and (ii) enabling two-way communication between the first vehicle and the location, wherein the arm member is structured to be selectively elongated and retracted by the drive system under control of the control system.

2. The system according to claim 1, wherein the arm member is structured to be coupled to a front portion of the first vehicle in a condition wherein the arm member is in a retracted state and is parallel to a front bumper of the first vehicle, and wherein the control system is structured to cause the drive system to pivot the arm member away from the front bumper and then cause the arm member to move to an elongated state.

3. The system according to claim 1, wherein the drive system is a pneumatic drive system.

4. The system according to claim 1, wherein the arm assembly further includes a wheel assembly provided at the distal end of the arm member.

5. The system according to claim 1, wherein the number of electronic devices includes a first microphone for capturing first audio signals and a first video camera for capturing first video signals, the first audio signals and the first video signals being at least part of the information provided to the control system, and wherein the control system includes a second microphone for capturing second audio signals from within the vehicle and a second video camera for capturing second video signals from within the first vehicle, wherein the system is structured to communicate the second audio signals and the second video signals to the remote assembly.

6. The system according to claim 5, wherein control system includes a first speaker for transmitting first audio based on the first audio signals and a first display for transmitting first video based on the first video signals, and wherein the remote assembly includes a second speaker for transmitting second audio based on the second audio signals and a second display for transmitting second video based on the second video signals.

7. The system according to claim 1, wherein the number of electronic devices includes an image capture device for capturing electronic images to be communicated to the control system.

8. The system according to claim 1, wherein the number of electronic devices includes a number of bar code readers for capturing bar code information to be communicated to the control system.

9. The system according to claim 1, wherein the number of electronic devices includes a magnetic stripe reader for capturing magnetic stripe information to be communicated to the control system.

10. The system according to claim 1, wherein the number of electronic devices includes a thermal imaging device for capturing thermal image information to be communicated to the control system.

11. The system according to claim 1, wherein the number of electronic devices includes a breath analysis device for capturing breath analysis information to be communicated to the control system.

12. The system according to claim 1, wherein the number of electronic devices includes an explosives detection device for capturing explosives detection information to be communicated to the control system.

13. The system according to claim 1, wherein the number of electronic devices includes an image capture device for capturing electronic images to be communicated to the control system, and wherein the control system includes facial recognition software structured to analyze the capture electronic images.

14. The system according to claim 1, wherein the number of electronic devices includes device for detecting controlled the presence of substances.

15. The system according to claim 1, wherein the arm assembly further includes a wheel assembly provided at the distal end of the arm member and connected to the remote assembly in a manner wherein the wheel assembly and the remote assembly are biased away from one another, and wherein the arm assembly further includes a housing member provided at the distal end of the arm member, the housing member being structured to cover the remote assembly and the wheel assembly when not in use.

16. The system according to claim 15, wherein the housing member is structured to be opened as a result of the arm member being elongated under the control of the control system.

17. The system according to claim 1, wherein the drive system includes a drive wheel assembly attached to a distal end of the telescoping arm member, the drive wheel assembly including a drive motor controlled by the control system and a number of wheels structured to be driven by the drive motor.

18. The system according to claim 17, wherein the drive wheel assembly includes a framework rotatably coupled to the distal end of the telescoping arm member, the system further comprising a second drive motor controlled by the control system and structured to selectively rotate the framework relative to the telescoping arm member.

19. The system according to claim 18, wherein the remote assembly is rotatably coupled to the distal end of the telescoping arm member, the system further comprising a third drive motor controlled by the control system and structured to selectively rotate the remote assembly relative to the telescoping arm member.

20. The system according to claim 1, wherein the drive system includes a drive motor provide at a distal end of the telescoping arm member, and a cable coupled to the drive motor and a distal portion of the telescoping arm member, wherein the drive motor is structured to retract the telescoping arm member using the cable.

21. The system according to claim 1, wherein the drive system and the remote assembly are part of a remotely operated vehicle controlled by the control system, the remotely operated vehicle being separable from and selectively dockable to the distal end of the arm member.

22. A method of conducting a vehicle traffic stop wherein a first vehicle stops a second vehicle, comprising:
pulling the first vehicle behind the second vehicle, the first vehicle having an arm member coupled thereto and having a remote assembly coupled to a distal end of the arm member;
elongating the arm member in a manner that positions the remote assembly adjacent a driver's side window of the second vehicle;
collecting information at or from a location adjacent the remote assembly and providing the information to the first vehicle; and
conducting two-way communications between the first vehicle and second vehicle using the remote assembly.

23. The method according to claim 22, wherein the arm member is coupled to a front portion of the first vehicle in a condition wherein the arm member is in a retracted state and is parallel to a front bumper of the first vehicle, and wherein the method includes pivoting the arm member away from the front bumper prior to elongating the arm member.

24. The method according to claim 22, wherein the collecting information comprises capturing information from a driver's license and a vehicle registration using one or more electronic devices forming a part of the remote assembly.

25. The method according to claim 24, wherein the one or more electronic devices comprise at least one of an image capture device, a barcode reader, and a magnetic stripe reader.

26. The method according to claim 22, wherein the two-way communications comprise two-way audio and two-way video.

* * * * *